United States Patent [19]
Organ

[11] Patent Number: 5,643,255
[45] Date of Patent: Jul. 1, 1997

[54] STEERABLE CATHETER WITH ROTATABLE TIP ELECTRODE AND METHOD OF USE

[75] Inventor: Leslie W. Organ, Charleston, S.C.

[73] Assignee: Hicor, Inc., Charleston, S.C.

[21] Appl. No.: 355,290

[22] Filed: Dec. 12, 1994

[51] Int. Cl.⁶ .................................................. A61B 50/04
[52] U.S. Cl. .................. 606/41; 606/34; 606/42; 607/122; 128/642
[58] Field of Search ................ 606/32–35, 37–42, 606/45–50; 607/115, 116, 100–102, 119, 122; 604/95; 128/642

[56] References Cited

U.S. PATENT DOCUMENTS

| | | |
|---|---|---|
| 4,955,382 | 9/1990 | Franz et al. ............... 607/122 |
| 5,125,896 | 6/1992 | Hojeibane . |
| 5,190,050 | 3/1993 | Nitzsche . |
| 5,242,441 | 9/1993 | Avitall ..................... 607/122 |
| 5,327,905 | 7/1994 | Avitall ..................... 606/45 |
| 5,357,956 | 10/1994 | Nardella .................. 128/642 |
| 5,398,683 | 3/1995 | Edwards et al. ........... 128/642 |

OTHER PUBLICATIONS

Leonard T. Blouin and Frank I. Marcus, *The Effect of Electrode Design on the Efficiency of Delivery of Radiofrequency Energy to Cardiac Tissue In Vitro*, PACE, vol. 12, Jan. 1989, Part II, pp. 136–143.

*Primary Examiner*—Angela D. Sykes
*Assistant Examiner*—Michael Peffley
*Attorney, Agent, or Firm*—McDermott, Will & Emery

[57] ABSTRACT

A catheter, used e.g. for cardiac ablation, has a handle, a shaft, and a J-bendable distal end containing tip and ring electrodes. The tip electrode is axially rotatable and has insulated and uninsulated portions. As the tip electrode is rotated, the impedance between it and a reference level is observed. When the impedance reaches a maximum, this indicates that the uninsulated portion lies against the tissue and the insulated portion faces the bloodstream. An electrogram can be taken from the electrode, or an ablation current can then be applied to it. Short circuiting of the signal or current through the blood is thus reduced.

29 Claims, 6 Drawing Sheets

STEERABLE CATHETER WITH ROTATABLE TIP ELECTRODE AND METHOD OF USE

FIELD OF THE INVENTION

This invention relates to an improved catheter which can be used both for applying a radio frequency (RF) ablation current to a body part, and for electrogram recording. The invention also relates to a method of applying an RF ablation current and a method of electrogram recording. An important application of the invention is in the field of cardiology.

BACKGROUND OF THE INVENTION

A healthy heart is normally caused to contract and relax in an orderly fashion by a spreading wave of electrical excitation originating from the sinoatrial (SA) node in the right upper atrium. The wave initiated at the SA node spreads over cardiac fibers until it reaches the atrioventricular (AV) node. The AV node then relays the wave over specialized cardiac fibers known as the bundle of His, to the ventricles. The cardiac fibers over which the impulses are conducted have a refractory period, so that once stimulated they cannot be restimulated for a short time period. This normally serves as a protective mechanism.

However some people are born with an accessory pathway of cardiac fibers extending from the ventricle near the area of the AV node back to the atrium. The accessory pathway allows the excitation wave from the AV node to retrograde or travel back to the atrium.

In some cases, if the retrograde wave reaches the atrium just after the end of a refractory period, it can then travel back to the AV node, stimulating the AV node prematurely and producing an oscillatory loop. Various other mechanisms, e.g. partial damage to atrial or ventricular heart muscle, can also result in an oscillatory loop. The oscillatory loop causes abnormally rapid heart action (tachycardia). This is usually self limiting, but in cases where it is not, it may be fatal. Therefore the condition requires treatment.

Tachycardia and other arrhythmias have sometimes been treated with medication. However the medication is not always effective and may have serious side effects.

A second method of treating the condition has been open heart surgery, to cut the tissue (e.g. the accessory pathway) which forms part of the feedback loop, thus opening the feedback loop. However open heart surgery is a serious and costly operation.

Therefore, for about the last fifteen years cardiologists have attempted to deal with the condition by inserting catheters containing electrodes into the interior of the heart. They have attempted to locate the accessory pathway or other tissue in question and then to apply RF energy to ablate the tissue by coagulation. The catheters are pushable and steerable, and are guided to the approximate location by x-rays for general guidance, and then by the use of electrograms to the exact location for fine localization. For example, the fibers known as the bundle of His, emanating from the AV node, are close to the accessory pathway, so cardiologists often look for electrograms with His activity to determine that the catheter is close to the accessory pathway.

Numerous catheters have been designed to perform the above functions. Examples are shown in U.S. Pat. No. 5,242,441 to Avitall, U.S. Pat. No. 5,125,896 to Hojeibane, and U.S. Pat. No. 5,190,050 to Nitzsche. Various designs compete on the basis of which is more easily steerable.

In an article by L. T. Blouin and F. I. Marcus, in Pace, Vol. 12, January, 1989, part 2, pages 136 to 143, it was disclosed that by insulating part of the tip of the catheter, and applying the bare (conductive) portion of the tip against dog ventricular muscle in vitro, larger lesions could be produced with lower RF power. However so far as is known, this technique has not been used to date in any practical catheters in animal or human subjects.

Regardless of which catheter is used to date, a serious problem has existed and currently exists in determining whether the catheter is in the right location to form an ablation. It is common for the surgeon to guide an ablation catheter to a location which is believed to be correct, then to apply RF power to create an ablation, and then to observe that nothing has happened. In that case the surgeon then moves the catheter elsewhere and tries again. In many of these cases, the catheter may in fact have been properly positioned, but because most of the tip of the catheter is bathed in blood rather than lying against the tissue, and since blood has a lower electrical impedance than the tissue, the RF power has effectively been short circuited through the blood and an adequate ablation has not been formed. Problems of this kind can greatly increase the time required for catheterization procedures and can decrease the likelihood of a successful result.

BRIEF SUMMARY OF THE INVENTION

Accordingly, it is an object of the present invention in one of its aspects to provide an improved catheter which can more readily be guided so that its tip can be placed in the desired location. In one aspect the invention provides a catheter comprising:
 (a) a handle,
 (b) a longitudinally extended shaft connected to said handle,
 (c) a distal end connected to said shaft, said distal end being bendable with respect to said shaft,
 (d) a tip electrode mounted on said distal end for axial rotation thereon, and at least one ring electrode mounted on said distal end adjacent to said tip,
 (e) said tip electrode having a conductive portion and an insulated portion,
 (f) first control means extending from said handle through said shaft and connected to said distal end for bending said distal end relative to said shaft,
 (g) second control means extending from said handle through said shaft to said tip electrode for axially rotating said tip electrode, so that said conductive portion of said tip electrode may be placed against tissue and said insulated portion may be oriented to face a patient's bloodstream.

In another aspect the invention provides a method of positioning a catheter in a desired manner over selected tissue within a patient, said catheter having a handle, a longitudinally elongated shaft connected to said handle, a distal end connected to said shaft, and an axially rotatable electrode on said distal end, said electrode having a conductive portion and an insulated portion, said method comprising:
 (a) moving said catheter so that said electrode is positioned over said selected tissue,
 (b) axially rotating said electrode,
 (c) observing the impedance between said electrode and a reference level as said electrode is axially rotated,
 (d) determining when said impedance reaches a peak value, said peak value being indicative that said conductive portion of said electrode is lying against said tissue, (e) and thereby positioning said electrode with said conductive portion lying against said tissue.

Further objects and advantages of the invention will appear from the following description, taken together with the accompanying drawings.

DETAILED DESCRIPTION OF PREFERRED EMBODIMENTS

Organization of Catheter

Figure 1:
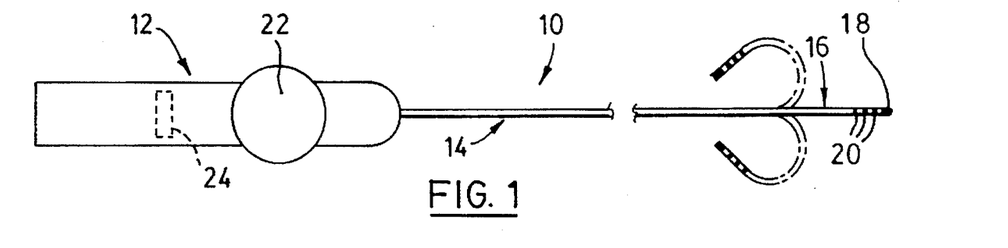
FIG. 1 is a top plan view of a catheter according to the invention.
Figure 2:
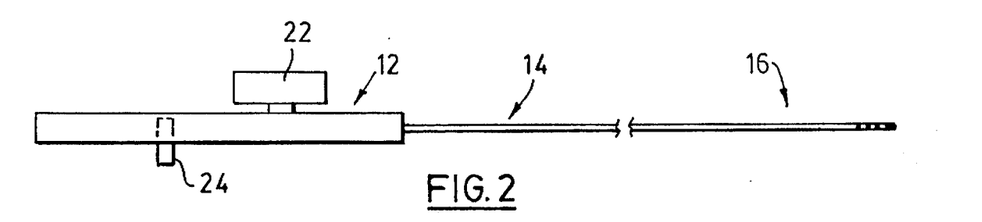
FIG. 2 is a side view of the catheter of FIG. 1.

An ablation catheter according to the invention is shown generally at 10 in FIGS. 1 and 2. Catheter 10 has three sections, namely a control handle 12, a shaft 14, and a distal or free end 16. The shaft 14 may typically be about 100 cm long and the distal end 16 may typically be about 8 cm long.

The distal end 16 typically contains four platinum-iridium alloy electrodes, namely a tip electrode 18 (which may be e.g. 4 mm long) and three ring electrodes 20. The ring electrodes are typically 1.5 mm long, with 2.5 mm spacing between their edges. However all dimensions mentioned can be varied as required.

Both the shaft 14 and the distal end 16 typically have an outside diameter of 7 French (2.34 mm) so that they can be guided through blood vessels into the heart.

The handle 12 contains a J-bending control knob 22 and an axial rotation control knob 24. Using knob 22 the distal end 16 can be deflected laterally into a J-shape (as shown in dotted lines in FIG. 1) to assist in steering the catheter toward a desired location. As will be explained, a portion of the tip 18 of the catheter is insulated, and the axial rotation control knob 24 is used to rotate the tip, to bring the bare (uninsulated) portion of the tip against the heart wall and the insulation toward the bloodstream once a desired location has been reached.

Distal Catheter End 16

Figure 3:
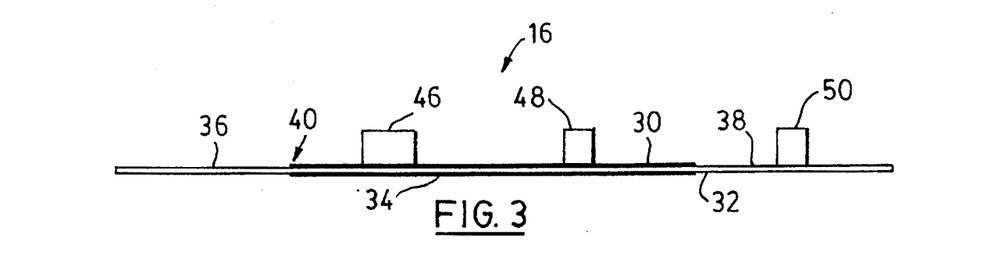
FIG. 3 is a side view of a portion of the distal end of the catheter of FIG. 1.
Figure 4:
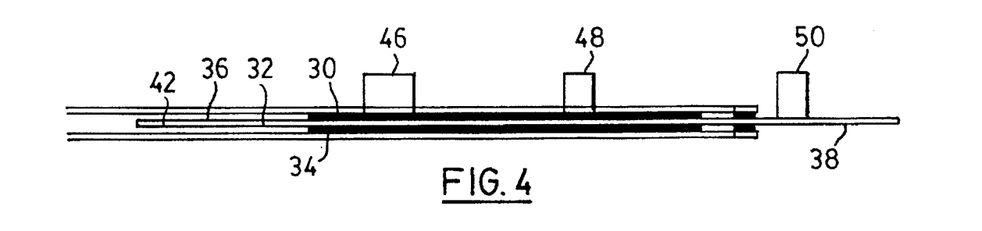
FIG. 4 is a view similar to that of FIG. 3 but with the pull wires included.
Figure 5:
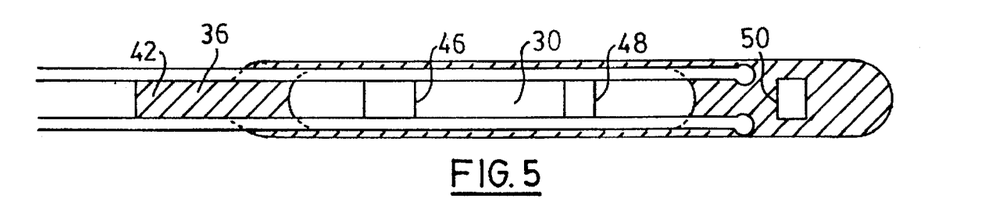
FIG. 5 is a top plan view of the portion of FIG. 4.

The catheter distal end 16 is shown in more detail in FIGS. 3 to 10 inclusive. Reference is first made to FIGS. 3 to 5, which show that the distal end 16 includes an assembly of three very thin planar stainless steel ribbons 30, 32, 34. Middle ribbon 32 is larger than ribbons 30, 34 and thus has a projecting proximal end 36 and a projecting distal end 38. Central ribbon 32 is also welded on each side to the proximal ends of upper ribbon 30 and lower ribbon 34, the weld locations being indicated at 40. The ribbons are not connected to each other except at the welds 40, so that they may slide at their distal ends. The ribbons thus determine a preferred bending direction (in a plane orthogonal to their flat surfaces) for the distal end 16 (i.e. J-bending).

Figure 7:
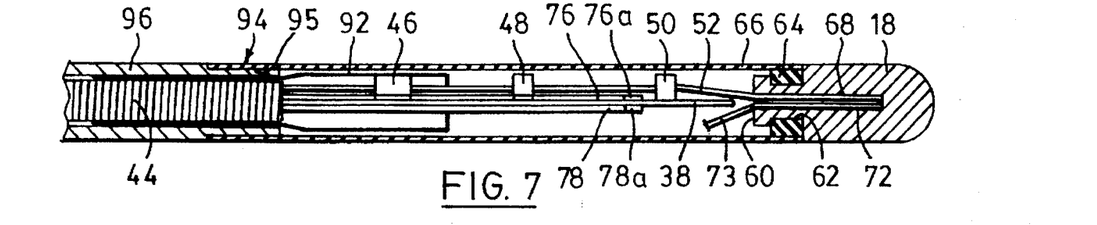
FIG. 7 is a side sectional view of the distal end of the catheter of FIG. 1.
Figure 8:
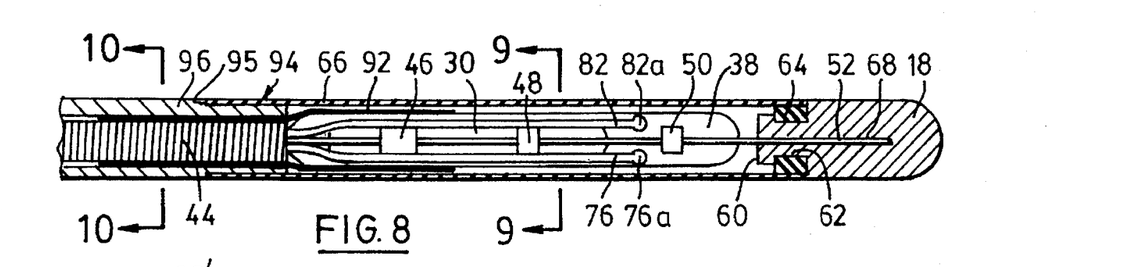
FIG. 8 is a top plan sectional view of the distal end of the catheter of FIG. 1.

The projecting proximal end 36 of the middle ribbon 32 narrows into an elongated tab 42 (FIG. 5) which inserts into a stainless steel coil 44 (FIGS. 7 and 8).

Three retainer rings 46, 48, 50 are attached (welded) to the ribbon assembly. Rings 46, 48 are attached to the upper ribbon 30 while ring 50 is attached to the projecting distal end 38 of middle ribbon 32. The rings 46, 48, 50 form a guide channel for a stainless steel torque wire 52 (FIGS. 7 to 10) which is coated with polytetrafluoroethylene (PTFE). The use of the rings results in minimal friction and column stiffness and yet allows free rotation of wire 52 as torque is applied to it (as will be described) to produce axial tip rotation. A length of polyimide or similar tubing 51 (FIG. 8A), attached e.g. by glue to upper ribbon 30, can be used in place of rings 46, 48, 50 to provide similar benefits. (In FIG. 8A primed reference numerals indicate parts corresponding to those of FIGS. 7 and 8.)

Torque wire 52 also serves as an electrical connection to the tip electrode 18.

The extent of tip rotation is made sufficient to bring the insulated portion (to be described) of the tip 18 to face the blood and then slightly beyond, regardless of the starting position of the tip and its direction of rotation. Preferably there is a range of axial rotation of ±300°.

Figure 6:
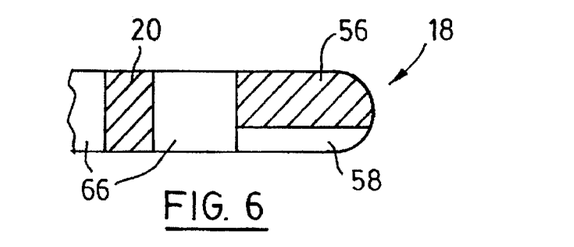
FIG. 6 is an enlarged view of the tip of the catheter of FIG. 1.

Reference is next made to. FIGS. 6 to 8 inclusive. As shown in FIG. 6, the tip electrode 18 is partially covered with an electrically insulating coating 56 (typically a polyimide coating), which coats more than 50% of the electrode surface. This leaves a single rectangular bare area 58, whose length is the length of the tip electrode (typically 4 mm) and whose width can be described in cross section by the extent of the arc in a direction circumferentially of the bare portion. The arc describing the lateral edges of the bare portion 58 will be less than 180° and is typically between 90° and 120°. However it can be less than 90°. The shape of the bare area may be modified, e.g. hourglass instead of rectangular.

The tip 18 is generally bullet shaped but at its proximal end includes a reduced diameter proximally extending portion 60 (FIGS. 7, 8) having a circumferential groove 62 therein. The groove 62 retains a sealing ring 64 made of silicone. An outer silicone sleeve 66, which forms a jacket for the catheter distal end, is pushed over sealing ring 64 to abut the proximal end of tip 18 and is then glued in position to provide a fluid tight seal against the tip 18.

The tip 18 also includes a central channel 68 in which the torque wire 52 is firmly soldered. Central channel 68 also houses a thermocouple heat sensor 72 (FIG. 7), from which lead wires 73 protrude. Alternatively, a thermistor heat sensor could be used.

The ring electrodes 20 (not shown in FIGS. 7 and 8 for simplicity) are glued to the outer silicone sleeve 66, and indent the sleeve so that their outer surfaces form a relatively smooth surface with that of the outer sleeve. Before gluing, ring electrode wires 74 (FIG. 9) which have been threaded through sleeve 66 and out appropriately positioned holes (not shown) in the sleeve are soldered to the ring electrodes. As the ring electrodes 20 are then moved into position over the sleeve 66, the wires 74 are pulled from the handle end of the sleeve leaving some slack in the wires 74 (as in thermocouple wires 73) to allow for bending and rotation. This operation is of course performed before the tip electrode 18 is attached.

Four stainless steel PTFE coated pull wires 76, 78, 80, 82 are provided, each terminating in an enlarged disk 76a, 78a, 80a, 82a. The enlarged disks are welded to the projecting distal end 38 of the middle stainless steel ribbon 32. Two pull wires are located on each side of the ribbon assembly as best shown in cross section in FIG. 9. The pull wires 76–82 serve to bend the assembly of ribbon 30, 32, 34, and hence the catheter distal end 16, in either of its two preferred directions for bending. It will be apparent that the bending will be in a J-shape.

Although not specifically shown in the drawings, torque wire 52 tapers in diameter at its distal end to provide increased flexibility to permit easier lateral deflection of the distal end 16 of the catheter.

Figure 10:
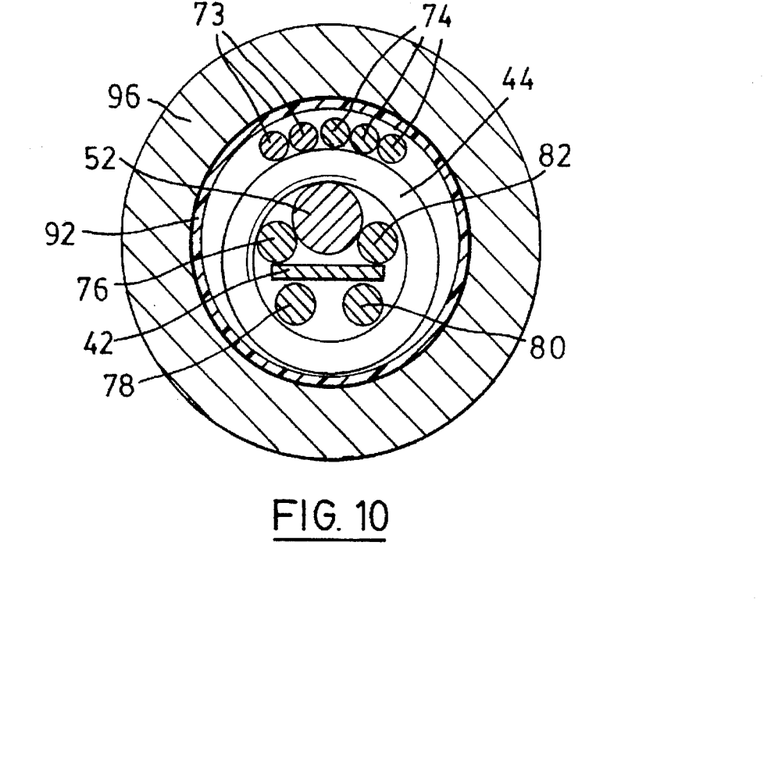
FIG. 10 is a cross-sectional view of the catheter of FIG. 1, taken along lines 10—10 of FIG. 8.

As best shown in FIGS. 7, 8 and 10, the pull wires 76–82, the tab section 42 of middle stainless steel ribbon 32, and the torque wire 52 are all inserted into the end of the stainless steel coil 44.

Figures 8A, 9:
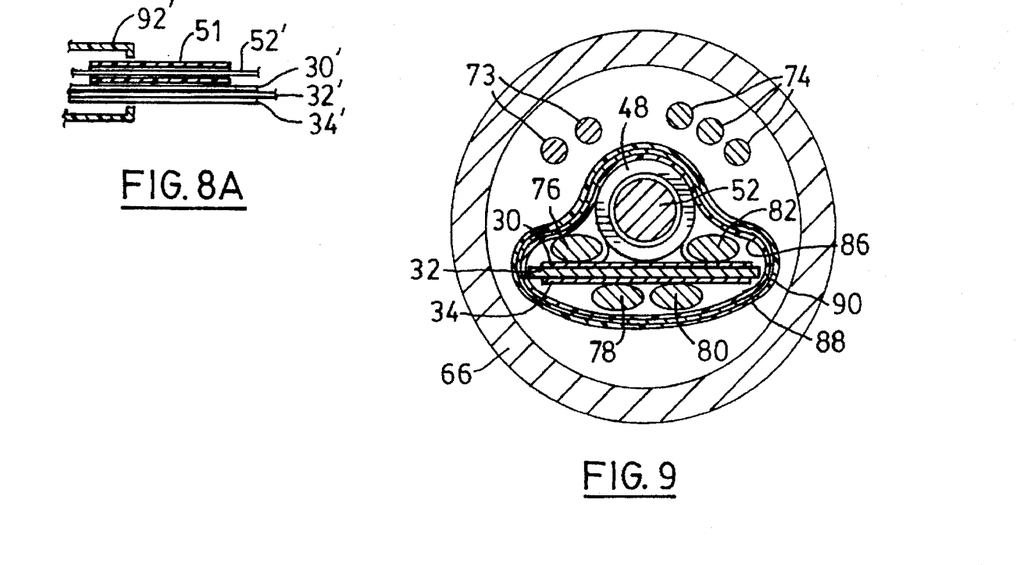
FIG. 8A shows a modification of the arrangement of FIGS. 7 and 8.
FIG. 9 is a cross-sectional view of the distal end of the catheter of FIG. 1, taken along lines 9—9 of FIG. 8.

As shown in FIG. 9, the pull wires 76–82, the ribbon assembly 30, 32, 34 and the torque wire 52 are held together adjacent the catheter distal end 16 with three layers of material (which for clarity are not shown in FIGS. 7 and 8). These layers consist of an inner layer of PTFE shrink tubing 86, a middle wrapping 88 of aramid fiber to provide strength against tearing during bending, and an outer layer of PTFE shrink tubing 90. The three layer covering extends distally about 0.025 inch beyond the ribbon assembly 30, 32, 34 and extends proximally to butt against the end of the stainless steel coil 44.

Located between the outer PTFE shrink tubing 90 and the silicone outer sleeve 66 are the thermocouple wires 73 and ring electrode wires 74 (FIG. 9).

A polyimide sleeve 92, shown in FIGS. 7 and 8 and in cross section in FIG. 10, bridges the junction of the catheter shaft 14 with the distal end 16, for reinforcing purposes. The sleeve 92 extends over the proximal end of the three layers 86, 88, 90 (which as mentioned are for clarity not shown in FIGS. 7, 8). As shown in FIGS. 7 and 8, the proximal end 94 of thin silicone sleeve 66 extends over a recessed area 95 of the catheter outer shaft wall 96 (which wall is described below).

Catheter Shaft

Figure 11:
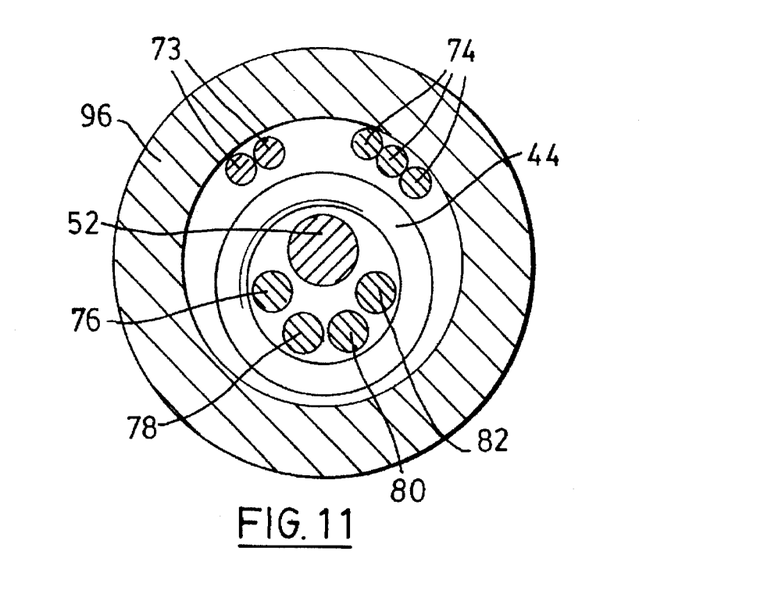
FIG. 11 is a cross-sectional view of the shaft of the catheter of FIG. 1.

The catheter shaft 14 is shown in cross section in FIGS. 10 and 11. FIG. 10, which is a cross section close to the junction of the shaft 14 with the catheter distal end 16, shows the tab section 42 of the middle stainless steel ribbon 32 inside the stainless steel coil 44.

The outer shaft wall 96 (FIGS. 10 and 11) is constructed of a stainless steel braid coated with a polyether block amide (PEBA)/nylon compound. This construction confers pushability and column stiffness to the shaft 14, while still allowing shaft flexibility. Wall 96 is fixed to the handle 12 and extends to a position over sleeve 92 (FIG. 7), to abut and support proximal end 94 of silicone sleeve 66 as described above.

Stainless steel coil 44 runs from inside the catheter handle 12, where it is rigidly fixed, along the entire length of the shaft (within wall 96) and slightly into the catheter distal end 16 (FIGS. 7 and 8). The distal end of the stainless steel coil 44 is the point against which the pull wires 76–82 produce the lateral bending of the catheter distal end 16.

As shown in FIG. 10, thermocouple wires 73 and ring electrode wires 74 are located between the stainless steel coil 44 and the outer shaft wall 96. The four pull wires 76–82 and the torque wire 52 are as mentioned contained within the coil 44.

Control Handle

Figure 12:
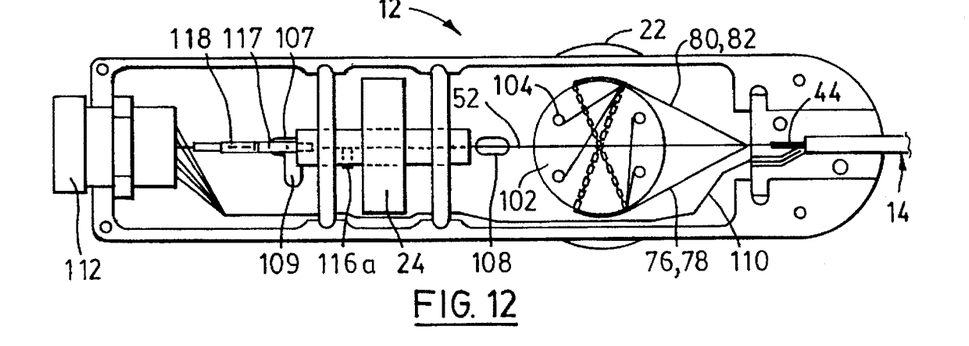
FIG. 12 is a diagrammatic top plan view, partly in section, of the handle for the catheter of FIG. 1.
Figure 13:
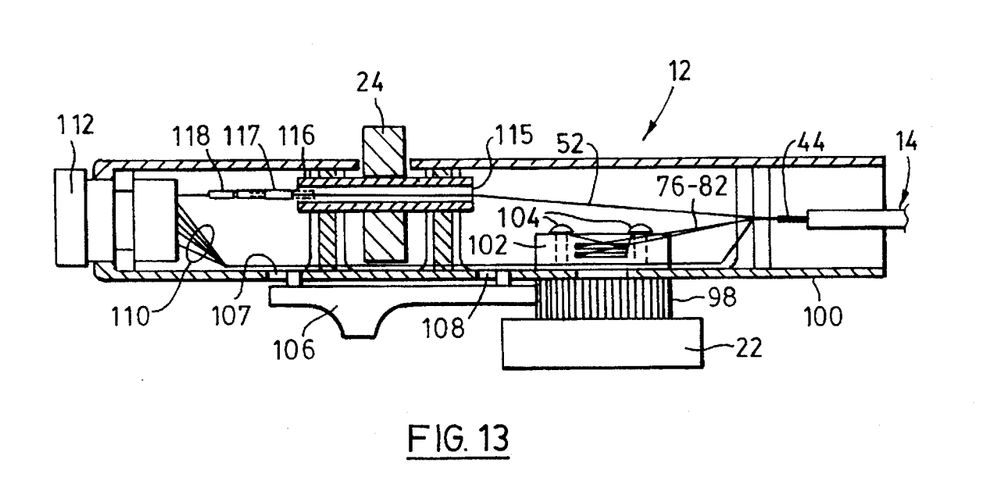
FIG. 13 is a side view, partly in section, of the handle of FIG. 12.

The details of the control handle 12 are shown in FIGS. 12 and 13. As shown, the J-bending control knob 22 includes a fluted or ridged shaft 98 rotatably mounted on handle wall 100 and having an interior shaft portion 102. The pull wires 76–82 are secured as shown to projections 104 from the interior shaft portion 102, so that turning of the knob 22 produces equal winding and unwinding of pull wire pairs. The resultant J-bending of the catheter distal end 16 is maintained with a locking lever 106. Lever 106 is adapted to slide forwardly in slots 107, 108 in the handle wall 100, to engage with the fluted or ridged control knob shaft 98. Locking lever 106 is then locked in position in the laterally extending portion 109 of slots 107 (which is L-shaped) to maintain the selected bend.

Figure 14:
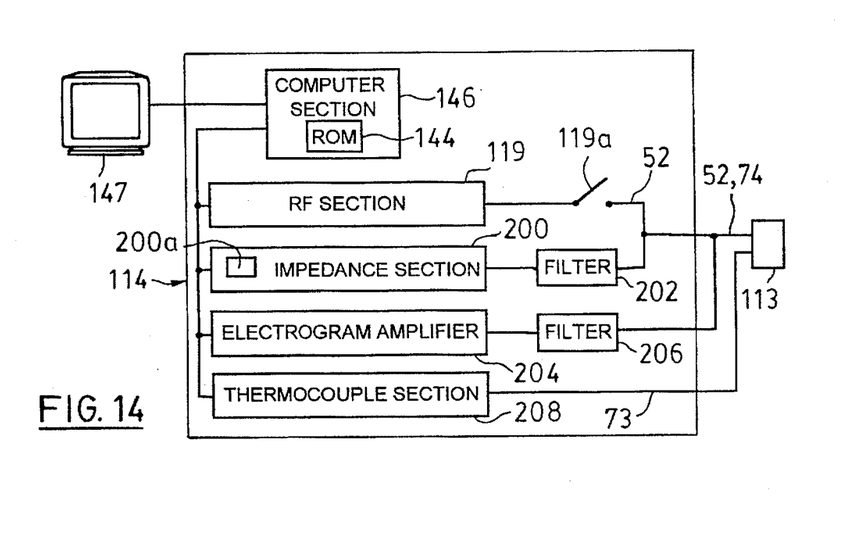
FIG. 14 is a diagrammatic view of a computer display and control for the catheter of FIG. 1.

A wire bundle 110, consisting of the thermocouple wires 73 and ring electrode wires 74, extends through the handle 12 and terminates in a male electrical connector 112 which may be connected by an appropriate female conductor and cable 113 to a computer based instrument 114 (FIG. 14). Torque wire 52 passes through an axial opening 115 in the acrylic (non-electrically conductive) shaft 116 of axial rotation control knob 24. Torque wire 52 is fixed to shaft 116 by a set screw 116a.

After passing through shaft 116, torque wire 52 terminates in a metal pin 117 which rotates within a fixed socket 118 which in turn is attached to the electrical connector 112. Electrical continuity of torque wire 52 is preserved in this manner, but other suitable methods of providing a rotating electrical connection may be provided. Ablation current (typically 500 KHz) when needed is supplied, under instrument 114 control, from radio frequency (RF) section 119 and through switch 119a to wire 52 and hence to tip electrode 18.

It will be seen from the above that whether the catheter distal end 16 is bent into a J-shape or is straight, the tip electrode 18 can be rotated through a considerable angle, essentially without altering the location of the tip electrode. In other words, if the tip electrode 18 is over particular tissue section, it will normally remain there even when the tip electrode 18 is rotated. The rotation does twist silicone sleeve 66, which is flexible and resilient for this purpose.

The Computer Instrument 114

Instrument 114 contains, in addition to the RF section 119, an impedance section 200. Impedance section 200 is conventional and generates a 50 KHz excitation current required to measure the impedance. It also produces an impedance measurement which is transmitted to a computer section 146 containing a CPU (not shown). Switch 119a allows the user to add RF current to the tip electrode to begin lesion making. However, impedance monitoring continues during application of the RF current, because a high frequency blocking filter 202 is located after the impedance section to filter out the RF current.

Instrument 114 also includes a standard electrogram amplifier 204 which is connected through a high frequency blocking filter 206 directly to leads 52, 74. Amplifier 204 receives the electrogram signals (whose frequency spectrum is all under 1 KHz, and mostly under 500 Hz), and amplifies these signals, and transmits them to the computer section 146 for recording and display. Filter 206 removes the higher frequencies of the impedance current and the ablation current. Thus the electronic signals and the impedance can be, and preferably are, monitored simultaneously, e.g. on monitor 147. (Note that the impedance section 200 need not be protected from the electrogram signals because their upper frequency limit (1 KHz) is appreciably lower than the 50 KHz used by the impedance section.)

Finally, instrument 114 includes a conventional thermocouple section 208 connected to thermocouple leads 73. Section 208 receives the thermocouple current, amplifies it, and transmits an appropriate signal to computer section 146 for recording and display.

The use of the catheter 10 will now be described.
Use

Figure 15:
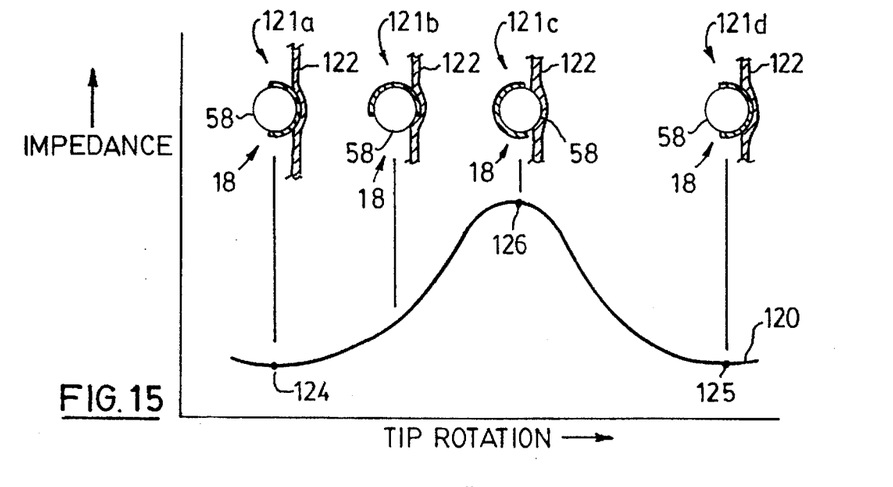
FIG. 15 is a graph showing variation of impedance versus rotation angle of the catheter tip.

Reference is made to FIG. 15, which shows a curve 120 of impedance (on the vertical axis) versus tip angle rotation (on the horizontal axis), for various angles of rotation of the catheter tip electrode 18. Shown above the plot in FIG. 15 are representations 121a to 121d of the catheter tip electrode 18 showing the bare (uninsulated) portion 58 of the tip in various positions with respect to the myocardial wall 122. The impedance shown is that between a reference electrode (not shown) connected to the patient and the wire 52 connected to the tip electrode 18.

As shown, when the uninsulated portion 58 faces the bloodstream (representations 121a and 121d), the impedance shown at 124, 125 is relatively low since blood is more conductive than myocardium. When the bare portion 58 is fully shielded from the bloodstream by lying directly against the myocardial wall 122 (representation 121c), the impedance reaches a peak as indicated at 126. Therefore the rotational position of the bare portion 58 of the catheter can be readily determined. When the impedance reaches a peak, then (assuming the catheter has been properly positioned over the arrhythmic pathway), RF energy can be efficiently and reliably applied to form the desired lesion.

In use, the impedance between catheter tip electrode 18 and the reference electrode (not shown) can be continually read on a graphic display such as that shown in FIG. 15. When the catheter has advanced to the desired location, as determined by electrograms picked up by ring electrodes 20 or tip electrode 18, the physician rotates the catheter tip using knob 24, meanwhile watching the display of FIG. 15, until the impedance has reached a peak. Impedance can also be displayed numerically or as a rising bar graph or other increasing graphical display. It can also be input to an audio source whose frequency increases as impedance increases, or can be displayed in any other desired manner. RF power is applied to the tip electrode 18 when impedance is greatest.

Figure 16:
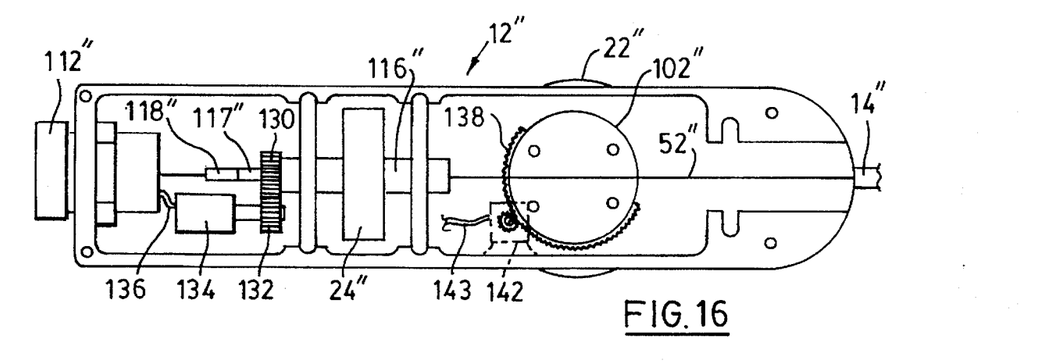
FIG. 16 is a top plan view of a modified handle for the catheter of FIG. 1.
Figure 17:
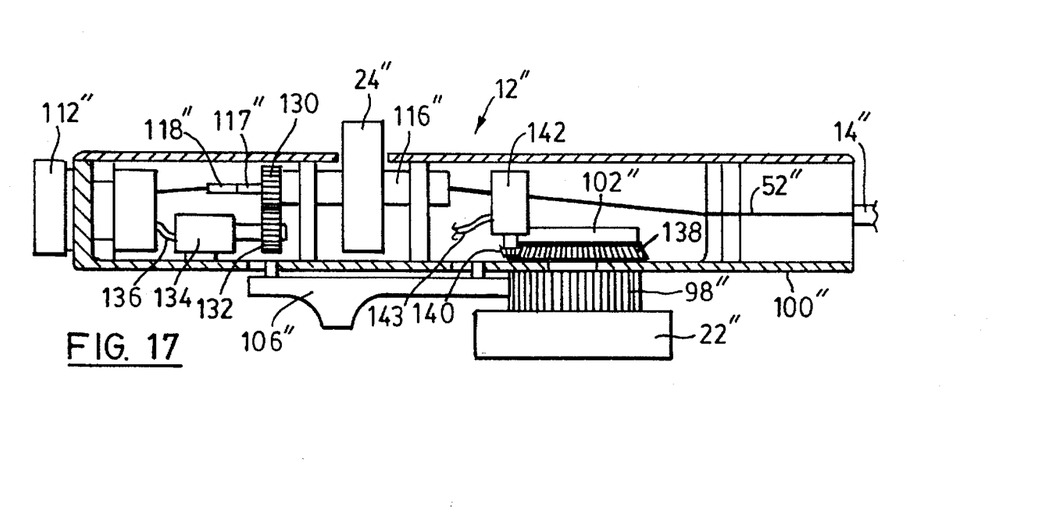
FIG. 17 is a side sectional view of the handle of FIG. 16.

If desired, potentiometers may be connected to knobs 22, 24 as shown in FIGS. 16, 17, where double primed reference numerals indicate parts corresponding to those of FIGS. 1 to 13. In FIGS. 16, 17 a spur gear 130 is formed on the end of shaft 116" of the axial rotation knob 24". Gear 130 drives a gear 132 on the shaft of potentiometer 134 mounted on wall 100". Potentiometer 134 has two leads 136 connected to connector 112".

Similarly, a semi-circular ring gear 138 is formed on interior shaft portion 102" of J-bending central knob 22". Gear 138 drives a bevel gear 140 connected to the shaft of a second potentiometer 142 having leads 143 connected to connector 112". The resistances of the potentiometers 134, 142 will indicate the axial rotation position of tip electrode 18 and the degree of J-bending of distal catheter end 16, respectively.

It will be realized that the relationship between the position of knob 24 and rotation of the tip electrode is not linear because friction on torque wire 52 within the distal catheter end 16 increases as J-bending increases. For example when the catheter distal end 16 is straight (no J-bending), one unit of rotation of knob 24 produces approximately one unit of axial rotation of the tip electrode 18. However when the catheter distal end is bent into a J-shape, there are significant torque losses and it may take (for example) two units of rotation of knob 24 to produce one unit of tip rotation. The actual relationships can be determined after the catheter has been manufactured, and can then be provided in the form of a look-up table in the read-only memory (ROM) 144 of the computer section 146 of the computer based instrument 114. The look-up table provides to the CPU in the computer section 146 the data representative of the actual degree of axial rotation, so that true tip rotation may be displayed graphically and/or numerically on a monitor 147.

Figure 18:
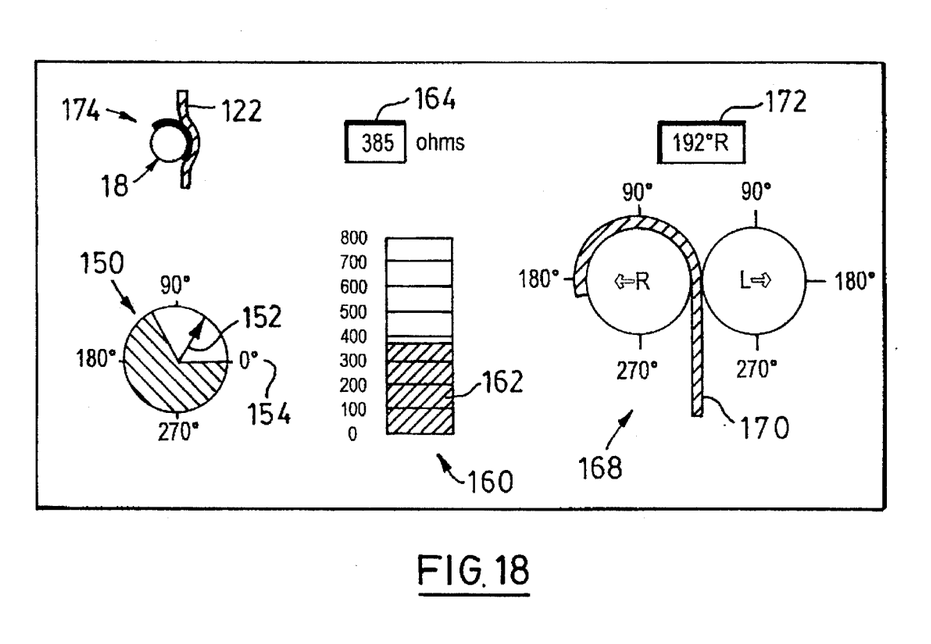
FIG. 18 shows a visual control display for the catheter of FIG. 1.

Several forms of display are possible, e.g. on the monitor 147. For example, as shown in FIG. 18, the tip electrode 18 may be displayed in cross-section as icon 150 with an arrow 152 indicating the number of degrees of rotation of the uninsulated portion 58 from a reference (unrotated) position 154 marked as 0°. The tip can as mentioned be rotated in either direction from the 0° position.

Above or beside the icon 150 for the tip rotation is a display 160 showing impedance. The impedance display consists of a shaded bar 162 which rises and falls as the impedance varies, with an ohm scale beside it on the vertical axis, and with the numeric value of the impedance at any given time displayed at 164. Thus, the operator of the catheter can see exactly how far the tip electrode 18 has been rotated from its 0° or reference position, and at the same time can see from display 160 (by rotating the tip electrode 18 back and forth) when the impedance reaches a peak.

The graphic display of FIG. 18 can also include a display 168 showing the amount of J-bending. This is indicated by an icon 170 representing the catheter distal end 16 and showing the amount of J-bending in the distal end 16. The amount of J-bending to the left or right is reproduced in the icon, with the alphanumeric value and the direction of bending displayed at 172.

An alternative or additional form of display for the rotational position of the tip electrode 18 is shown as icon 174 in FIG. 18. The icon 174 is simply one of the displays 121a to 121d from FIG. 15 and displays the rotational relationship of the tip 18 relative to the tissue wall 122. As the impedance rises or falls, the displayed position of the tip 18 rotates. Such display can be generated by the computer instrument 114, which can be programmed to rotate the representation of tip 18 dependent on whether the impedance (indicated by graph 120) is at a peak or valley, or between those two extremes. The orientation of the insulated portion 56 (whether it is at the top or bottom of the drawing) can be determined by the program from whether the impedance rises or falls when the tip is rotated clockwise or counterclockwise.

While the impedance is normally measured between the tip electrode 18 and a reference electrode connected elsewhere to the patient, the impedance can if desired be measured between the tip electrode 18 and any of the ring electrodes 20. However it is preferred to use a larger reference electrode located elsewhere on the patient for more consistent results.

While the catheter described is particularly useful for ablation purposes, it may also be used simply for monitoring purposes, to detect signals from any of its electrodes (to record electrograms), i.e. it may be used as a diagnostic catheter. Diagnostic catheters are normally identical to ablation catheters except that the tip electrode 18 is shorter (e.g. only 2 mm long) in a diagnostic catheter. There may also be more than four electrodes. In diagnostic mode electrograms may be recorded between the tip electrode 18 and a reference electrode, or between the tip electrode 18 and any of the ring electrodes 20, or between any ring electrode and any other ring electrode or a reference electrode.

Figure 19:
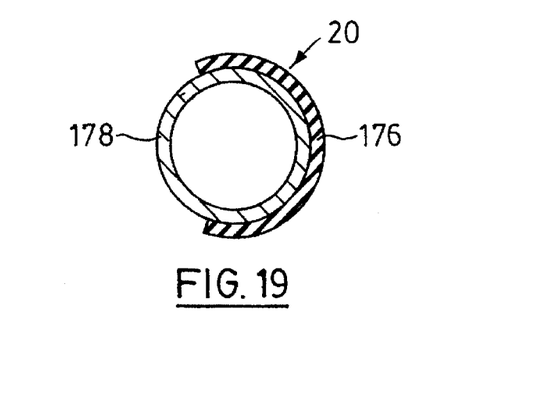
FIG. 19 is a side view of a modified ring electrode for the catheter of FIG. 1.

Further, if desired one or all of the ring electrodes 20 may be partially insulated, such insulation being shown at 176 in FIG. 19. The arcuate extent of the uninsulated portion 178 may have the same range as the uninsulated portion 58 of the catheter tip electrode 18.

In use of this last version, as the catheter is being positioned a four channel read-out can be displayed on a multichannel monitor or on monitor 147. If one of the ring electrodes 20, for example, begins picking up an electrogram feature of interest, indicating that such ring electrode is over a desired site, then the catheter as a whole, or simply that ring electrode, can be switched to impedance mode. Alternatively as mentioned, by use of the electronic filtering described, impedance and electrograms can be monitored simultaneously. Since as mentioned the frequency spectrum for the electrogram is under 1 KHz, while the impedance excitation current is 50 KHz, filtering suffices in each section to remove unwanted signal. In impedance mode, the impedance is read between the catheter electrode in question and the reference electrode (or between each catheter electrode and the reference electrode if all four channels are switched to impedance mode).

When impedance mode is activated, the impedance between the selected ring and the reference electrode is displayed, or four channels of impedance can be displayed, between each catheter electrode and the reference electrode. The catheter distal end 16 is then rotated to bring the uninsulated portion 178 of the ring in question as fully as possible against the tissue wall, at which time the impedance will be a maximum and the signal being picked up by the ring in question will be optimized in size and quality, i.e. more detail will be visible in the wave form of the electrogram signal. The increase in size and detail of the electrogram signal as the catheter is rotated confirm the information from the impedance signal that the uninsulated portion 178 is fully against the tissue wall.

Even if the rings are not partially insulated, the electrogram signal from tip electrode 18 will show an increase in size and quality when the tip is rotated so that its uninsulated portion is fully against the tissue wall, and this will constitute confirmation that the tip has been rotated to the correct position. Thus, if desired, one channel of impedance and four channels of electrograms (one electrogram channel for each electrode) can be displayed simultaneously (where only the tip is partially insulated), or (where the rings are also partially insulated) several impedance channels (up to four) and up to four channels of electrograms can all be simultaneously displayed.

It will be seen that rotating the partially insulated tip so that no uninsulated portion is exposed to the circulating blood prior to applying lesion current has a number of advantages for an ablation catheter. The procedure prevents loss of RF current to the blood and thereby increases the efficiency of the lesion making process. It also improves the reliability of the process because of the greater certainty that a lesion has been made. In addition, because less RF current is needed, it reduces the risk of blood clot formation from the RF current, and it also reduces possible risk of changes in blood coagulation factors produced by exposure to the RF current.

For a diagnostic catheter a major advantage of tip rotation is that the signal detected can be optimized. In all cases the use of impedance readings allows the operator to rotate the distal end to the desired axial position. Rotation is realized best with tip electrode 18, and progressively less with ring electrodes 20 as their distance from the tip increases since their rotation is produced by twisting of the outer silicone sleeve 66, to which they are attached.

Impedance readings are dependent on waveform frequency and current magnitude. (The current magnitude dependence can be eliminated if a tetrapolar impedance measurement system is used, but this would be difficult within the body.) The 50 KHz waveform from impedance section 200 is supplied at a constant current level by constant current source 200a to prevent variations in impedance due to current magnitude, thereby making this system more accurate. This can be useful during RF ablations using ablation catheters with either insulated or non-insulated electrode tips where changes in impedance will be followed or observed as a method of determining whether or not a satisfactory lesion has been produced. Typically the heating from RF current produces an initial liquefaction of tissue, causing a slight decrease in impedance (e.g. from an initial 150 ohms down to 130 ohms), followed by a larger impedance rise as the liquefied tissue coagulates into a solid (e.g. up to 300 ohms.) The initial fall in impedance is an important signal that good lesion formation will follow, indicating the desirability of monitoring impedance before application of the RF current because the decrease is often small and could be missed if no pre-lesion value was available. Current use is to obtain impedance measurements only during lesion making by taking the ratio of rms (root-mean-square) RF voltage to rms RF current. Typically, RF current changes during lesion making—this factor itself affecting impedance readings—and therefore is likely to obscure the initial true fall in impedance.

With the invention, where impedance measuring current is supplied at a different frequency (e.g. 50 KHz) from the ablation current (e.g. 500 KHz), and because of the filter 202, impedance can be monitored both before and during the lesion making process, as described above.

While preferred embodiments of the invention have been described, it will be appreciated that various changes may be made within the scope of the invention without departing from the invention itself.

I claim:

1. A catheter comprising:
   (a) a handle,
   (b) a longitudinally extended shaft connected to said handle,
   (c) a distal end connected to said shaft, said distal end being bendable with respect to said shaft,
   (d) a tip electrode mounted on said distal end for axial rotation thereon, and at least one ring electrode mounted on said distal end adjacent to said tip,
   (e) said tip electrode having a conductive portion and an insulated portion, (f) a first control extending from said handle through said shaft and connected to said distal end and being operable for bending said distal end relative to said shaft, (g) a second control extending from said handle through said shaft to said tip electrode and being operable for axially rotating said tip electrode, so that said conductive portion of said tip electrode may be placed against tissue and said insulated portion may be oriented to face a patient's bloodstream.

2. A catheter according to claim 1 wherein said tip electrode is generally bullet shaped and has a circumference, said conductive portion extending over not more than 180° of said circumference.

3. A catheter according to claim 2 wherein said conductive portion extends over between 90° and 120° of said circumference.

4. A catheter according to claim 2 wherein said conductive portion extends over not more than 90° of said circumference.

5. A catheter according to claim 1 wherein said distal end is covered with a resilient flexible sleeve and said tip electrode is connected to said sleeve, so that the portion of said sleeve adjacent said tip electrode rotates with said tip electrode and so that the connection between said tip and said sleeve reduces the likelihood of fluid leakage into said catheter.

6. A catheter according to claim 1 and including impedance measuring means adapted to be coupled to said tip electrode and to a reference electrode which is adapted to be connected to said patient, for measuring the impedance between said tip electrode and said reference electrode.

7. A catheter according to claim 6 and including means coupled to said impedance measuring means for displaying said impedance on a visual display.

8. A catheter according to claim 7 and including axial rotation measurement means coupled to said second control for determining from the operation of said second control the degree of axial rotation of said tip electrode from a reference position, and means coupling said axial rotation measurement means to said visual display for displaying on said visual display said impedance and an indication of the degree of axial rotation of said tip electrode from said reference position.

9. A catheter according to claim 7 and including computer means coupled to said impedance measuring means for determining from said impedance measuring means the axial rotational position of said tip electrode relative to a tissue surface against which said tip electrode lies, said computer means being coupled to said visual display for displaying on said visual display said impedance and an indication of said axial rotational position of said tip electrode relative to said tissue surface against which said tip electrode lies.

10. A catheter according to claim 6 or 7 wherein said tip electrode has a circumference and said conductive portion extends over not more than 120 degrees of said circumference.

11. A catheter according to claim 7, 8 or 9 and including bending measurement means coupled to said first control for determining from the operation of said first control the amount of bending of said distal end, and means coupling said bending measurement means to said visual display for displaying on said visual display an indication of said amount of bending of said distal end.

12. A catheter according to claim 6 and including display means, and computer means coupled between said display means and said impedance measuring means for causing said display means to display in one of an alternative and a simultaneous manner, the impedance between said tip electrode and a reference level, and an electrogram signal received from said tip electrode.

13. A catheter according to claim 1 and including means coupled to said tip electrode for monitoring the impedance between said tip electrode and a reference level and for determining from said impedance the axial rotational position of said tip electrode relative to a tissue surface against which said tip electrode lies, a visual display, said means coupled to said tip electrode being coupled to said visual display for displaying on said visual display an indication of said axial rotational position of said tip electrode relative to said tissue surface against which said tip electrode lies.

14. A catheter according to claim 1 or 6 and including means coupled to said tip electrode for supplying an ablation current to said tip electrode.

15. A catheter according to claim 1 wherein said handle includes measuring means connected to said first and said second controls to monitor operation of said first and second controls, and computer means connected to said measuring means for determining therefrom the amount of axial rotation of said tip electrode and for determining the amount of bending of said distal end.

16. A catheter according to claim 1 wherein said distal end includes three ring electrodes, said catheter further including computer means coupled to at least some of said ring electrodes and said tip electrode, said catheter further including display means coupled to said computer means for providing a multi-channel display, one channel for said at least some ring electrodes, said computer means including means for controlling said display means for said display means to display in one of an alternative and a simultaneous manner, the impedance between at least one of said ring and tip electrodes and a reference level, and an electrogram signal received from between any pair of electrodes selected from said ring and tip electrodes.

17. A catheter according to claim 1 and including electrogram receiving means connected to at least one of said electrodes for receiving electrogram signals of a first frequency range therefrom, and impedance signal means connected to at least said tip electrode for generating and applying thereto an impedance measuring signal of a second frequency outside said first frequency range, and first filter means connected between said electrogram receiving means and the electrodes to which said electrogram receiving means is connected for blocking said impedance signal from said electrogram receiving means.

18. A catheter according to claim 17 and including means connected to said tip electrode for supplying an ablation current to said tip electrode, said ablation current being of a frequency outside said first frequency range and different from said second frequency, and second filter means connected between said impedance signal means and said electrodes to which said impedance signal means is connected, for blocking said ablation current from reaching said impedance signal means, said first filter means also blocking said ablation current from reaching said electrogram measuring means.

19. A catheter according to claim 18 and including display means, and computer means coupled to said display means and to said impedance signal means and to at least some of said electrodes for controlling said display means for displaying simultaneously the impedance between at least said tip electrode and a reference level, and at least one of said electrogram signals.

20. A catheter according to claim 1 wherein said distal end includes a plurality of thin ribbons having flat surfaces and having proximal ends connected together and coupled to said shaft and distal ends free to slide relative to each other, to constrain bending of said distal end to a plane orthogonal to said flat surfaces, and wherein said means for rotating said tip includes a plurality of rings mounted on said ribbon assembly, and a torque wire extending through said shaft and through said rings and connected to said tip.

21. A catheter according to claim 1 wherein said distal end includes a plurality of thin ribbons having flat surfaces and having proximal ends connected together and coupled to said shaft and distal ends free to slide relative to each other, to constrain bending of said distal end to a plane orthogonal to said flat surfaces, and wherein said means for rotating said tip includes a flexible tube mounted on said ribbon assembly, and a torque wire extending through said shaft and through said tube and connected to said tip.

22. A catheter according to claim 21 wherein said torque wire is electrically conductive and is electrically connected to said tip for carrying electrical signals from said tip and for conducting lesion current to said tip.

23. A method of positioning a catheter in a desired manner over selected tissue within a patient, said catheter having a handle, a longitudinally elongated shaft connected to said handle, a bendable distal end connected to said shaft, a first control connected to said distal end for bending said distal end relative to said shaft to steer said catheter, an axially rotatable electrode on said distal end, and a second control connected to said electrode for axially rotating said electrode, said electrode having a conductive portion and an insulated portion, said method comprising:

(a) steering said catheter so that said electrode is positioned over said selected tissue, (b) operating said second control to axially rotate said electrode while said electrode is positioned over said selected tissue, (c) monitoring the impedance between said electrode and a reference level as said electrode is axially rotated, (d) determining when said impedance reaches a peak value, said peak value being indicative that said conductive portion of said electrode is lying against said tissue, and;

(e) thereby positioning said electrode with said conductive portion lying against said tissue.

24. A method according to claim 23 wherein said electrode is a catheter tip electrode.

25. A method according to claim 24 and including the step, after said step (e), of applying an ablation current to said tip electrode.

26. A method according to claim 23 and including the step of observing an electrogram signal received from said electrode during said step (a), and when a desired signal is received, then performing said steps (b) to (e), and after said step (e), then again observing said signal received from said electrode.

27. A method according to claim 25 wherein said electrode is a catheter tip electrode.

28. A method according to claim 23 wherein said electrode is a ring electrode.

29. A method according to claim 23 or 25 wherein said tissue is heart tissue.

* * * * *